United States Patent [19]

Tanabe

[11] 4,145,616
[45] Mar. 20, 1979

[54] X-RAY SOURCE ASSEMBLY
[75] Inventor: Kaname Tanabe, Yokohama, Japan
[73] Assignee: Tokyo Shibaura Electric Co., Ltd., Kawasaki, Japan
[21] Appl. No.: 838,968
[22] Filed: Oct. 3, 1977
[30] Foreign Application Priority Data
  Oct. 5, 1976 [JP] Japan .................................. 51-119578
[51] Int. Cl.$^2$ ........................ H01J 35/16; H05G 1/04
[52] U.S. Cl. ..................................... 250/505; 250/405; 250/520
[58] Field of Search ................. 250/505, 520, 503, 405
[56] References Cited
  U.S. PATENT DOCUMENTS

| 2,497,755 | 2/1950 | Berggren | 250/503 |
| 3,558,890 | 1/1971 | Yanagshita | 250/505 |
| 3,743,836 | 7/1973 | Holland et al. | 250/405 |

Primary Examiner—Alfred E. Smith
Assistant Examiner—T. N. Grigsby
Attorney, Agent, or Firm—Cushman, Darby & Cushman

[57] ABSTRACT

X-ray source assembly includes an X-ray tube comprising a filament for emitting an electron beam, a grid electrode for focusing the electron beam from the filament and a rotating anode-target on which the electron beam impinges thereby to generate an X-ray. The X-ray tube is installed in a housing having an X-ray radiation port for emitting the X-ray emanated from the rotating anode-target. To the X-ray radiation port there is attached a collimator which is secured to a support arm. The housing is supported by the support arm and is made swingable about an actual focal spot formed of the electron beam on the anode-target. When the housing is swung, the axis of the collimator swings about the actual focal spot relative to the axis of the X-ray tube in the plane including the axis of the X-ray tube and the axis of the X-ray radiation port, thereby changing the angle between the axis of the collimator and the axis of the X-ray radiation port. The size of the actual focal spot is varied by the grid electrode. Thus, said angle and the size of the actual focal spot determine the size of an effective focal spot, i.e. the actual focal spot as seen in the axial direction of the collimator.

5 Claims, 8 Drawing Figures

X-RAY SOURCE ASSEMBLY

This invention relates to an X-ray source assembly, particularly to an X-ray source assembly which can vary the size of the effective focal spot of X-ray.

Generally an X-ray tube is constituted by a filament for emitting thermoelectrons, an anode-target on which the thermoelectrons from the filament impinge and a glass envelope in which the filament and anode-target are disposed in an air-tight fashion. The spot on the anode-target where the thermoelectrons impinge is called "focus" or more precisely "actual focal spot". As well known, the X-ray tube is provided with a beam focusing electrode (or "grid") which controls the thermoelectrons emitted from the filament thereby to change the size of the actual focal spot.

An X-ray emanated from the actual focal spot of the anode-target is directed to an object through a collimator or a beam limiting device which acts as an iris diaphragm to control the size of the X-ray spot on the object. The focal spot on the anode-target as seen fromm the object in the axial direction of the collimator is called "effective focal spot". Namely the effective focal spot is a projection of the actual focal spot on a plane normal to the axis of the collimator. The size of the effective focal spot is an important factor to the quality of the resultant X-ray photos, i.e., the image resolution of X-ray photography.

Generally, the smaller the effective focal spot is, the more the image resolution is improved. Further, a square effective focal spot provides a better image resolution than a rectangular one. Of course, the effective focal spot can be made smaller if the actual focal spot is made smaller by the beam focusing electrode. But the width of the actual focal spot changes, while the length changes little. As a result, the ratio of the width to the length of the effective focal spot is varied, and the effective focal spot, if made small, is not square-shaped in many cases. For this reason, the desired image resolution cannot always be obtained. d Hitherto, among many X-ray source assemblies providing different effective focal spots, one assembly providing a specific effective focal spot of the most suitable size for a specific object had to be selected and used to take an X-ray photo of the object. There has been invented an X-ray source assembly which has, as disclosed in U.S. Pat. No. 2,942,126, two filaments and an anode-target with two concentric annular target tracks, this providing two effective focal spots of different sizes. But this X-ray source assembly is defective in that since the two actual focal spots are formed at different positions (i.e. two annular target tracks), the X-rays from the actual focal spots irradiate different regions of the object.

The object of this invention is to provide an X-ray source assembly which can vary the size of the effective focal spot to a desired one and produce a sufficient X-ray output.

The X-ray source assembly according to this invention comprises an X-ray tube including a cathode provided with an electron-focusing electrode and a filament for emitting a condensed electron beam, an anode-target with an electron-receiving surface facing the cathode and a glass envelope in which the cathode and anode-target are disposed; a housing in which the X-ray tube is installed and which has an X-ray radiation port for emitting X-ray from the X-ray tube; and a collimator kept in contact with the X-ray radiation port, the axis of the collimator passing a point where the electron beam impinges on the electron-receiving surface and being swingable about said point relative to the axis of the X-ray radiation port in the plane including the axis of the X-ray tube and the axis of the X-ray radiation port, thereby controlling the size of X-ray irradiation region.

This invention can be more fully understood from the following detailed description when taken in conjunction with the accompanying drawings, in which.

With reference to the accompanying drawings the preferred embodiments of the X-ray source assembly according to this invention will be described.

Figure 1:
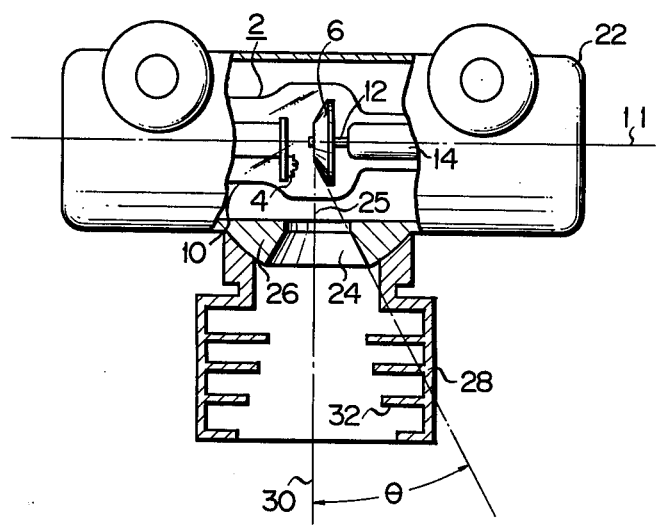
FIG. 1 is a partially cross-sectional front view of an embodiment of the X-ray source assembly according to this invention.

The X-ray source assembly shown in FIG. 1 is provided with an X-ray tube 2. The X-ray tube 2 comprises a cathode 4, an anode-target 6 facing the cathode 4 and a glass envelope 10 in which the cathode 4 and anode-target 6 are housed in air-tight fashion. The anode-target 6 is a rotating one, as shown in FIG. 1. But an anode-target of another type may be used as well. The anode-target 6 is mounted on a rotatable stem 12, which is attached to a rotor 14. The anode-target 6 has its electron-receiving surface inclined to the axis 11 of the X-ray tube 2 usually at 5° to 20°.

Figure 2:
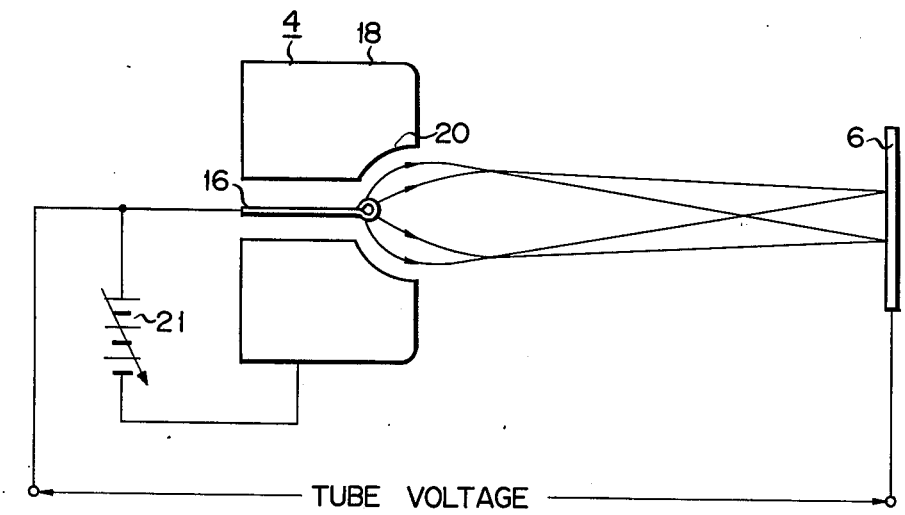
FIG. 2 is a schematical view of the beam focusing electrode of the X-ray tube of the X-ray source assembly shown in FIG. 1.

As schematically illustrated in FIG. 2, the cathode 4 comprises a filament 16 for emitting thermoelectrons, a beam focusing electrode 18 (hereinafter called "grid") for focusing and controlling the thermoelectrons from the filament 16, and a throat 20. In case the anode-target 6 is a rotating one, it is desirable that the cathode 4 emits an electron beam which forms on the electron-receiving surface of the anode-target 6 a rectangular actual focal spot extending in the radial direction of the anode-target 6. To this end, the filament 16 is formed into a coil with a diameter of, for example, 0.5 to 30mm and a length of, for example, 3 to 20mm and disposed radially in the direction perpendicular to the axis 11 of the X-ray tube 2.

The throat 20 has a rectangular shape which corresponds to that of the filament 16 and is disposed radially also in the direction perpendicular to the axis 11 of the X-ray tube 2. The electron beam from the throat 20 is diverged or converged by the grid 18 according to the bias voltage applied to the grid 18 from a bias voltage source 21.

The X-ray tube 2 is disposed in a housing 22 as shown in FIG. 1. The housing 22 has an X-ray radiation port 24, and the axis 25 of which passes the above-mentioned actual focal spot. To the flange portion 26 of the housing 22, which defines the X-ray radiation port 24, a collimator 28 is attached to control the direction of X-ray radiation and the size of X-ray radiation field.

Figure 3:
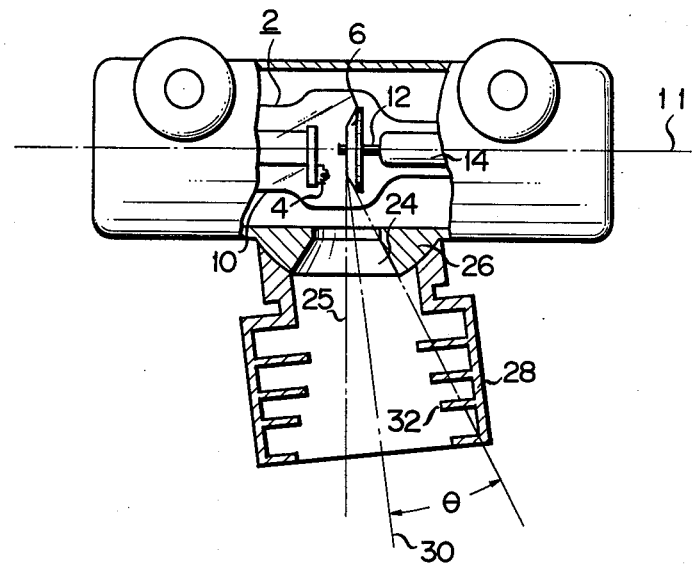
FIG. 3 is a partially cross-sectional front view of the X-ray apparatus shown in FIG. 1, showing how the collimator of the X-ray source assembly is moved.

As shown in FIG. 3, the axis 30 of the collimator 28 can swing at 5° to 20° relative to the axis 11 of the X-ray tube 2 in the plane including the axis 11 of the X-ray tube 2 and the axis 25 of the X-ray radiation port 24, with the actual focal spot as a swing center. The flange portion 26 of the housing 22 has a smooth convex surface, and the center of curvature of which is, for example, the actual focal spot. The collimator 28 has a smooth concave surface which fits to the convex surface of the flange portion 26. The collimator 28 has many plates 32, which are movable and cooperate to change the size of the X-ray radiation field.

Figure 4:
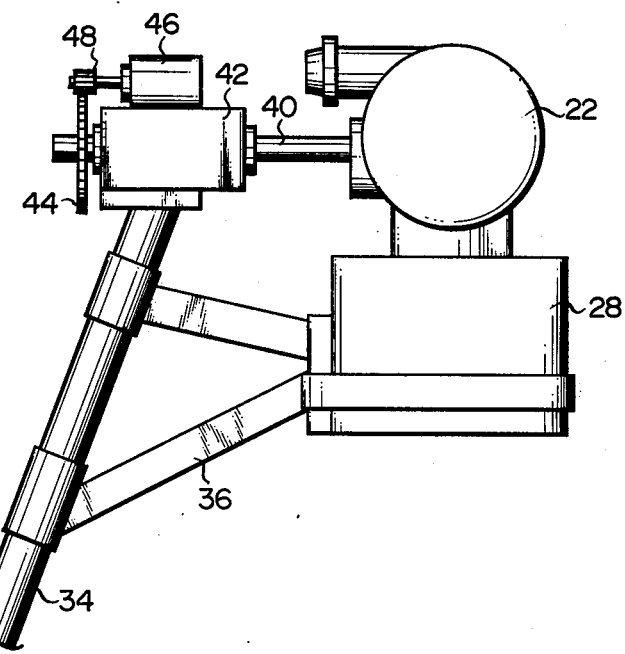
FIG. 4 is a side view of the X-ray source assembly shown in FIG. 1, provided with a mechanism for swinging the housing of the X-ray source assembly.

The collimator 28 is secured to a support arm 34 through a frame member 36 as illustrated in FIG. 4. In this embodiment, the housing 22 is made to swing with the actual focal spot as a swing center, thereby to incline the axis 25 of the X-ray radiation port 24 to the axis 30 of the collimator 28. To make the housing 22 swing in this manner, a shaft 40 is secured to the housing 22, extends from the swing center of the housing 22, and is supported by a bearing 42 which is fixed to the support arm 34. To the shaft 40 there is fixed a gear 44 put in engagement with another gear 48 which is secured to a motor 46 mounted on the support arm 34. Thus, driven by the motor 46, the shaft 40 is rotated to swing the housing 22. In this way the axis 11 of the X-ray tube 2 is inclined at a desired angle to the axis 30 of the collimator 28. The shaft 40 may not be secured to the housing 22, but extend into the housing 22 through a hole (not shown) and be secured to a plate (not shown) which supports the X-ray tube 2. If this is the case, the X-ray tube 2, not the housing 22, is swung as the shaft 40 is rotated by the motor 46.

Figure 5:
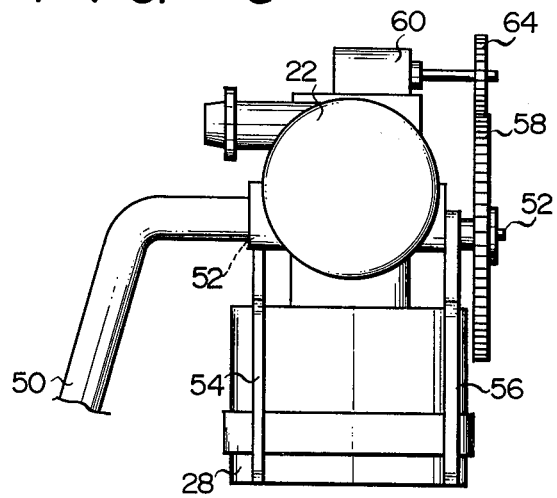
FIG. 5 is a side view of the X-ray source assembly shown in FIG. 1, provided with a mechanism for swinging the collimator.

The collimator 28 may be swung instead of the housing 22 as shown in FIG. 5. In this embodiment, the housing 22 is secured to a support arm 50. A pair of shafts 52 are fixed to the both sides of the housing 22 in alignment with each other. Their common axis passes the swing center of the collimator 28. A pair of arms 54 and 56 are swingably attached to the shafts 52, respectively and are secured to the collimator 28. The arms 54 and 56 are secured to a gear 58 which is rotatable on one of the shafts 52 and which is put in engagement with another gear 64 fixed to the shaft 62 of a motor 60 mounted on the housing 22. When driven by the motor 60, the arms 54 and 56 are swung around the shafts 52, and the collimator 28 eventually swings about the shafts 52.

As mentioned above, it is possible with the X-ray source assembly according to this invention to vary properly the angle defined by the axis 11 of the X-ray tube 2 and the axis 30 of the collimator 28 and thus the angle defined by the axis 30 of the collimator 28 and the electron-receiving surface of the anode-target 6 of the X-ray tube 2. As a result, the size of the effective focal spot can be changed to any desired one. In addition, since the actual focal spot on the electron-receiving surface is rectangular and extends in the radial direction of the anode-target 6 in case the anode-target 6 is a rotating one, the X-ray source assembly can produce a great output for the following reasons.

Figure 6:
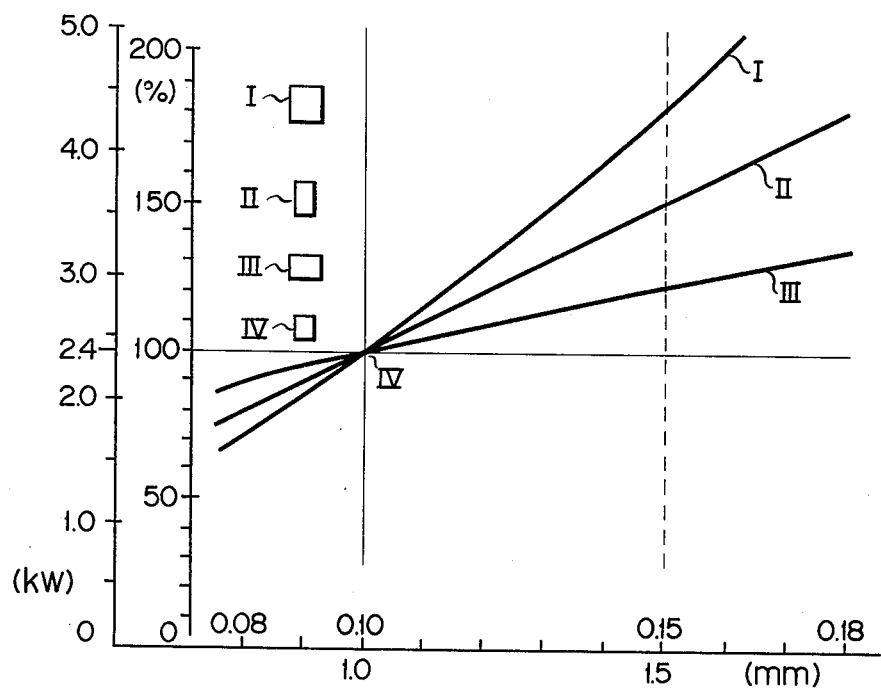
FIG. 6 is a graph showing the relationship between the shape and size of an actual focal spot and the maximum input power to the X-ray tube of the X-ray source assembly shown in FIG. 1.

FIG. 6 is a graph indicating the relationship between the maximum input power to the X-ray tube 2 and the shape and size of the actual focal spot. On the ordinate of the graph the maximum input power (kW) is plotted. Plotted on the auxiliary ordinate is the ratio (%) of the maximum input power in the case of a rectangular actual focal spot formed in the X-ray tube 2 to the maximum input power in the case of a square actual focal spot (0.1 × 0.1 mm) formed in the X-ray tube 2. Plotted on the abscissa is the width (mm) and length (mm) of the actual focal spot formed in the X-ray tube.

In the graph of FIG. 6, line I shows how the maximum input power changes as the width and length of a square actual focal spot (0.1 × 0.1 mm) are equally varied as illustrated by FIG. I. Line II teaches how the maximum input power changes as only the length of the square actual focal spot (0.1 × 0.1 mm) is varied as depicted by FIG. II. Line III indicates how the maximum input power changes as only the width of the square actual focal spot (0.1 × 0.1 mm) is varied as shown in FIG. III. Thus point IV where these three lines I, II and III intersect shows the maximum input power in the case of a square actual focal spot (0.1 × 0.1 mm) in the X-ray tube 2. Here, "width" of the actual focal spot means the dimension measured in the circumferential direction of the spot, and "length" means the dimension measured in the radial direction of the spot.

As indicated in the graph, the larger the actual focal spot is, the greater becomes the maximum input power of the X-ray tube 2. Further, the graph teaches that the permissible maximum input power becomes greater when the length of the actual focal spot is increased rather than when the width thereof is increased. In other words, an actual focal spot in which the length is larger than the width permits a greater maximum input power than does an actual focal spot having the same area in which the length is smaller than the width. This is because the thermoelectrons emitted from the grid 16 impinge on a given region of the rotating anode-target 6 more frequently if the width of the actual focal spot is larger than the length. Thus, the anode-target is more liable to melt in this case as compared with in the case that the width of the actual focal spot is smaller than the length, provided that the input power to the X-ray tube 2 is constant.

As mentioned above, the actual focal spot is rectangular and extends in the radial direction of the anode-target 6. Thus the maximum input power to the X-ray tube 2 is greater than otherwise. Consequently, the maximum output of the X-ray tube 2 can be greater than that of the tube having the rectangular actual focal spot extending in the circumferential direction of the anode-target 6.

Figure 7:
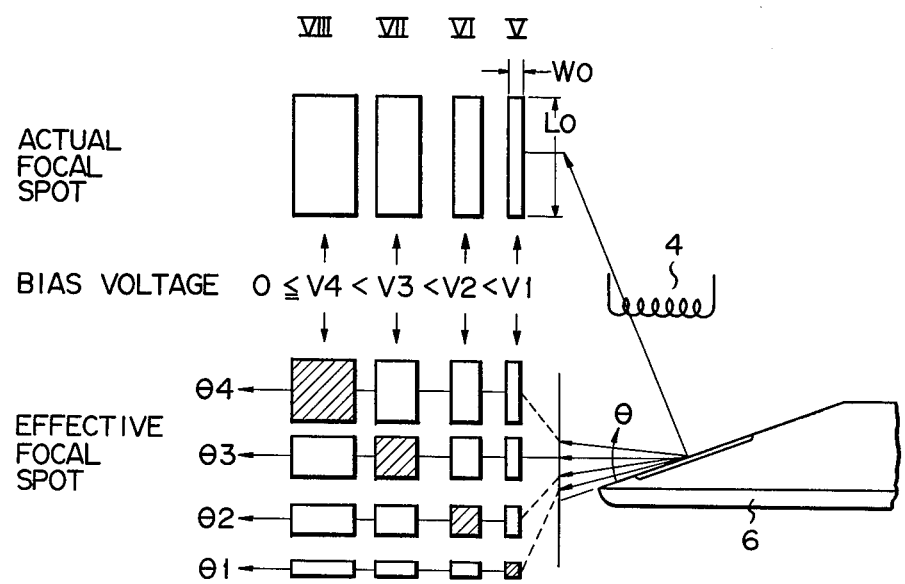
FIG. 7 shows various sizes and shapes in which an actual focal spot and an effective focal spot may take in the X-ray source assembly in accordance with some factors; and X-ray source

FIG. 7 shows the relationship between the shape of the actual focal spot and that of the effective focal spot, i.e. the shape of the actual focal spot as seen in the direction of X-ray radiation or along the axis 30 of the collimator 28. The width W of the effective focal spot is nearly equal to that of the actual focal spot. Its length L is expressed as Lo sin $\theta$, where "Lo" denotes the length of the actual focal spot and "$\theta$" denotes the angle defined by the axis 30 of the collimator 28 and the electron-receiving surface of the anode-target 6. Thus, the length L of the effective focal spot is determined by the length Lo of the actual focal spot and the angle $\theta$ between the axis 30 and the electron-receiving surface of the anode-target 6. The actual focal spot may have various widths Wo according to the bias voltage V applied to grid 16, as illustrated by FIGS. V, VI, VII and VIII.

The bias voltage V can be changed to $V_1$, $V_2$, $V_3$ or $V_4$, and the angle $\theta$ between the axis 30 of the collimator 28 and the electron-receiving surface of the anode-target 6 can also be varied to $\theta_1$, $\theta_2$, $\theta_3$ or $\theta_4$. As a result, the effective focal spot may have any one of various shapes as shown in FIG. 7. Among the various effective focal spots shown in FIG. 7 the square ones which are hatched provide good image resolution in X-ray photography and thus are desirable.

Figure 8:
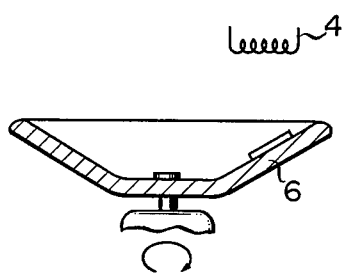
FIG. 8 is a partially cross-sectional side view of a rotating anode-target which differs from that of the X-ray source assembly shown in FIG. 1.

In the above-mentioned embodiments the anode-target 6 is an ordinary rotating one. Instead it may be such a disc-like anode-target as illustrated in FIG. 8 or may be such a rotating anode-target with two concentric annular target tracks as disclosed in U.S. Pat. No. 2,942,126.

What is claimed is:

1. An X-ray source assembly comprising an X-ray tube including a glass envelope, a cathode installed in the glass envelope and provided with an electron-focusing electrode and a filament for emitting a focused electron beam, and an anode-target installed in the glass envelope and provided with an electron-receiving surface facing the cathode; a housing in which said X-ray tube is disposed and which has an X-ray radiation port for radiating X-ray emanated from the X-ray tube; and a collimator kept in contact with the X-ray radiation port, the axis of the collimator passing a point where the electron beam impinges on the electron-receiving surface and being swingable about said point relative to the axis of the X-ray radiation port in the plane including the axis of the X-ray tube and the axis of the X-ray radiation port, thereby controlling the size of X-ray radiation field.

2. An X-ray source assembly according to claim 1, wherein said housing is secured to a support means, and said collimator is swung by a swing mechanism.

3. An X-ray source assembly according to claim 1, wherein said collimator is secured to a support means, and said housing is swung by a swing mechanism.

4. An X-ray source assembly according to claim 1, wherein said anode-target of the X-ray tube having the cathode is a rotating anode-target.

5. An X-ray source assembly according to claim 4, wherein said cathode emits an electron beam, which forms on said electron-receiving surface a rectangular actual focal spot extending in the radial direction of said anode-target.

* * * * *